(12) United States Patent
Boyle et al.

(10) Patent No.: US 7,344,549 B2
(45) Date of Patent: Mar. 18, 2008

(54) EXPANDABLE CAGES FOR EMBOLIC FILTERING DEVICES

(75) Inventors: William J. Boyle, Fallbrook, CA (US); William J. Harrison, Temecula, CA (US); Benjamin C. Huter, Murrieta, CA (US); Scott J. Huter, Temecula, CA (US); Paul F. Muller, San Carlos, CA (US); John E. Papp, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 435 days.

(21) Appl. No.: 10/066,314

(22) Filed: Jan. 31, 2002

(65) Prior Publication Data
US 2003/0144685 A1    Jul. 31, 2003

(51) Int. Cl.
*A61M 29/00* (2006.01)
(52) U.S. Cl. .................................................. 606/200
(58) Field of Classification Search ................ 606/113, 606/114, 127, 159, 200
See application file for complete search history.

(56) References Cited

U.S. PATENT DOCUMENTS

| 5,192,286 | A  | 3/1993  | Phan et al.    |
|-----------|----|---------|----------------|
| 5,658,296 | A  | 8/1997  | Bates et al.   |
| 5,779,716 | A  | 7/1998  | Cano et al.    |
| 5,814,064 | A  | 9/1998  | Daniel et al.  |
| 5,910,154 | A  | 6/1999  | Tsugita et al. |
| 5,954,745 | A  | 9/1999  | Gertler et al. |
| 6,001,118 | A  | 12/1999 | Daniel et al.  |
| 6,053,932 | A  | 4/2000  | Daniel et al.  |
| 6,059,814 | A  | 5/2000  | Ladd           |
| 6,142,987 | A  | 11/2000 | Tsugita        |
| 6,152,946 | A  | 11/2000 | Broome et al.  |
| 6,168,604 | B1 | 1/2001  | Cano           |
| 6,179,861 | B1 | 1/2001  | Khosravi et al.|
| 6,203,561 | B1 | 3/2001  | Ramee et al.   |
| 6,214,026 | B1 | 4/2001  | Lepak et al.   |
| 6,245,089 | B1 * | 6/2001 | Daniel et al. ............... 606/200 |
| 6,264,663 | B1 | 7/2001  | Cano           |
| 6,277,139 | B1 | 8/2001  | Levinson et al.|

(Continued)

OTHER PUBLICATIONS
US 6,348,062, 02/2002, Hopkins et al. (withdrawn)

*Primary Examiner*—Kevin T. Truong
(74) *Attorney, Agent, or Firm*—Fulwider Patton LLP

(57) ABSTRACT

A self-expanding cage for use in conjunction with an embolic filtering device includes a circumferential member adapted to expand from an unexpanded position to a expanded position within the patient's body vessel. A proximal strut and distal strut are attached to the circumferential member to form the cage. A plurality of proximal and distal struts may be attached the circumferential member. Additionally, a second circumferential member can be attached to the first circumferential member. Each circumferential member can be connected by a single or a plurality of connecting struts. One embodiment of the cage utilizes a single wire to form to the cage. A delivery system attached to the single wire cage moves the cage and its associated filter element between the expanded and unexpanded positions through relative movement of the distal delivery system. This can be accomplished by either torquing the guide wire onto which the expandable cage is mounted or by longitudinally moving a tubular member which forms part of the delivery system longitudinally in relation to the guide wire.

15 Claims, 9 Drawing Sheets

U.S. PATENT DOCUMENTS

| | | |
|---|---|---|
| 6,336,934 B1 | 1/2002 | Gilson et al. |
| 6,346,116 B1 | 2/2002 | Brooks et al. |
| 6,371,970 B1 | 4/2002 | Khosravi et al. |
| 6,540,722 B1 | 4/2003 | Boyle et al. |
| 6,656,202 B2 * | 12/2003 | Papp et al. .................. 606/200 |
| 6,660,021 B1 * | 12/2003 | Palmer et al. .............. 606/200 |

* cited by examiner

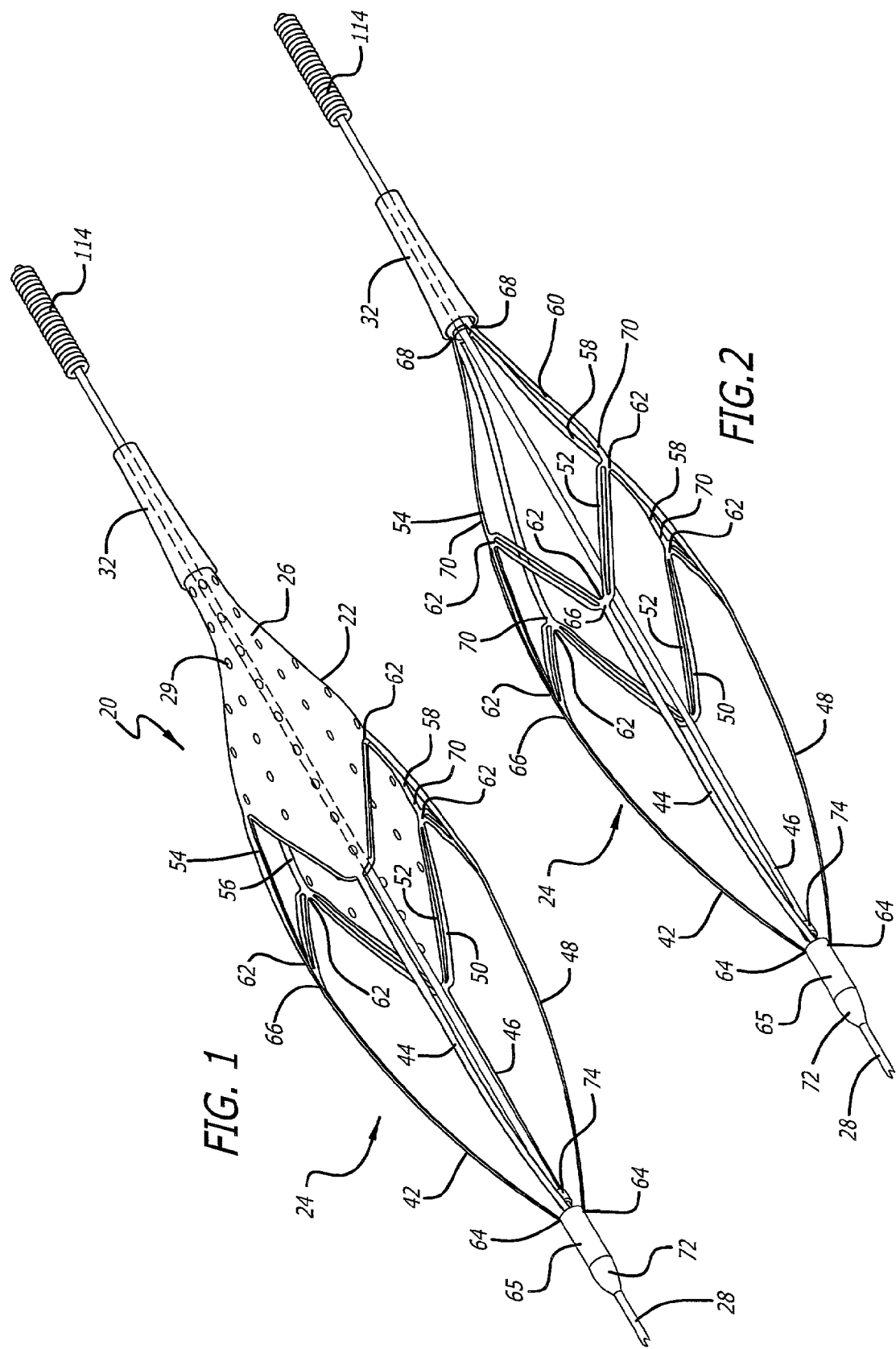

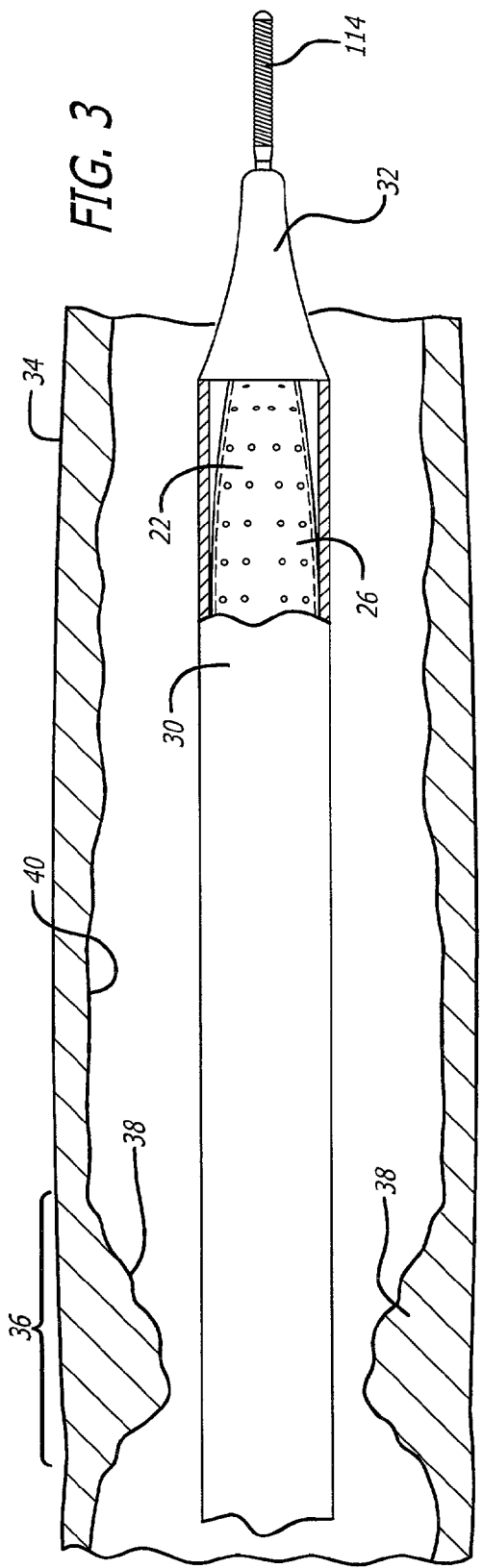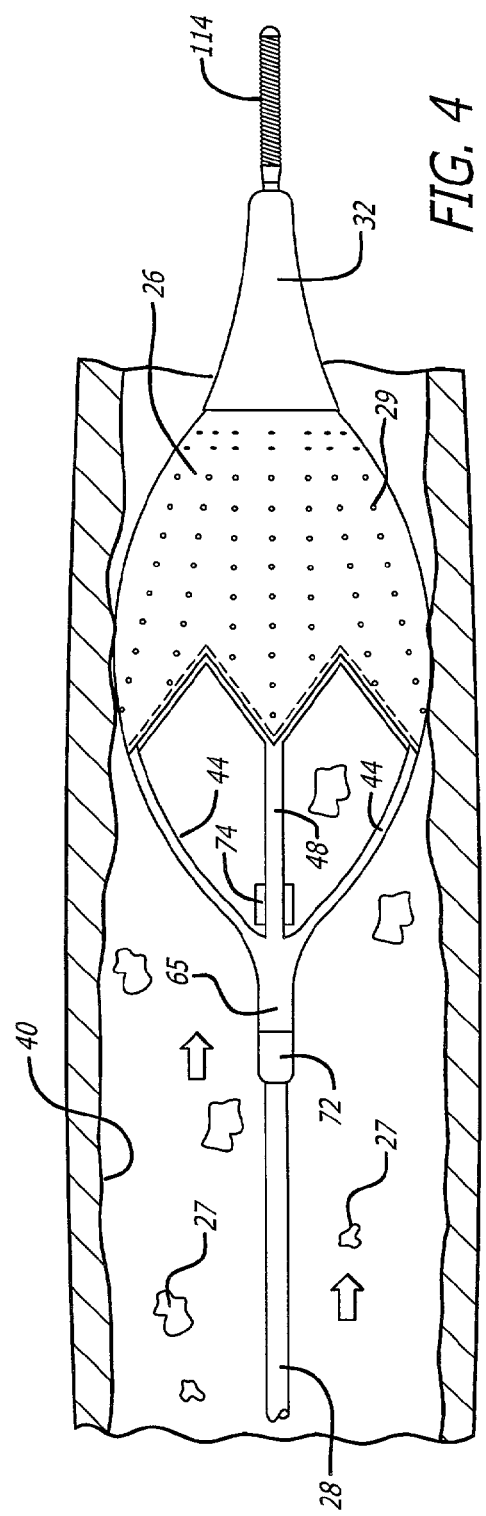

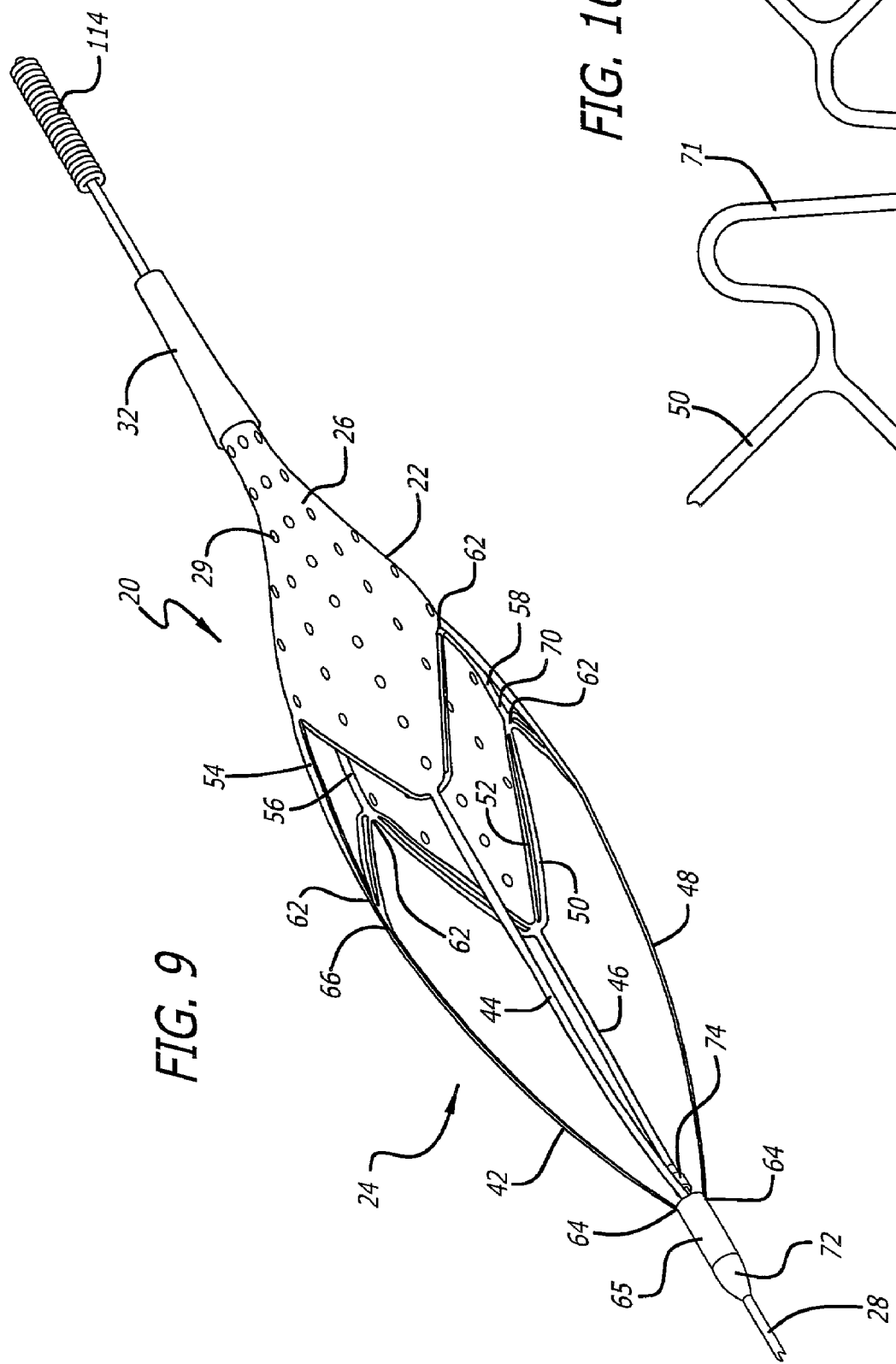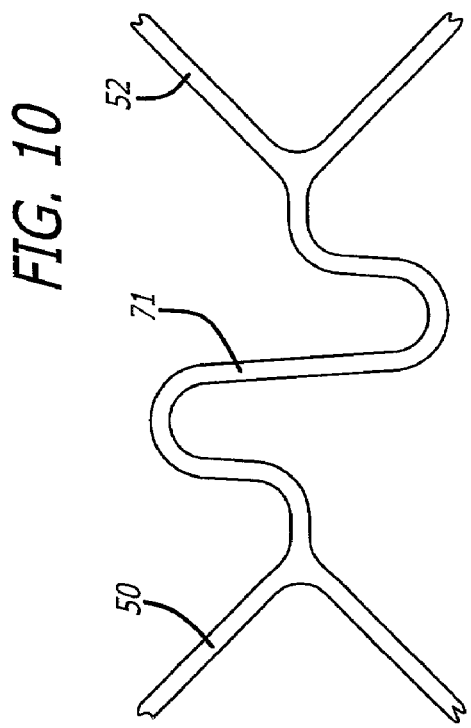

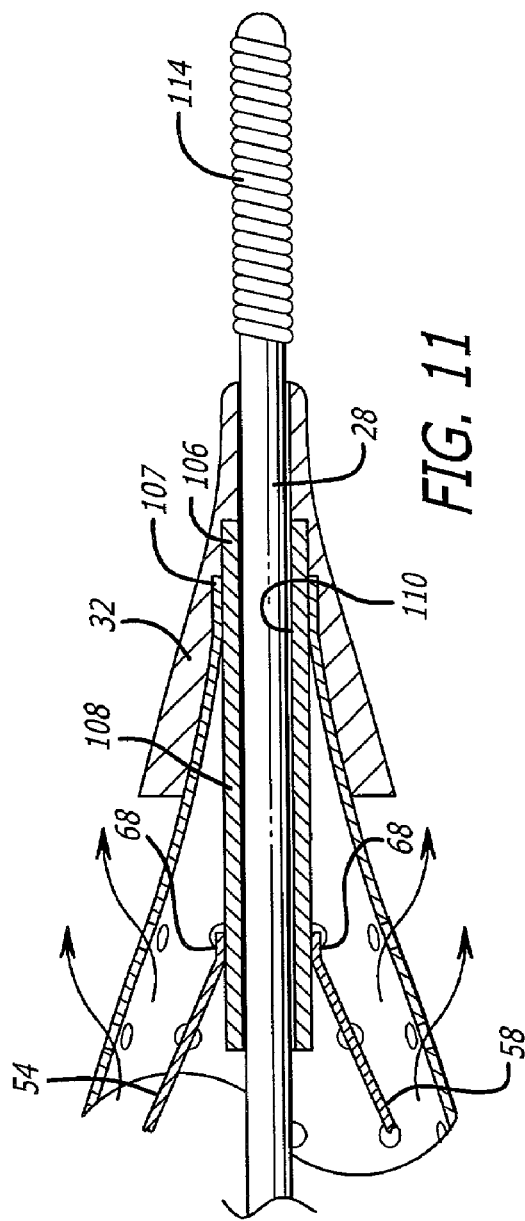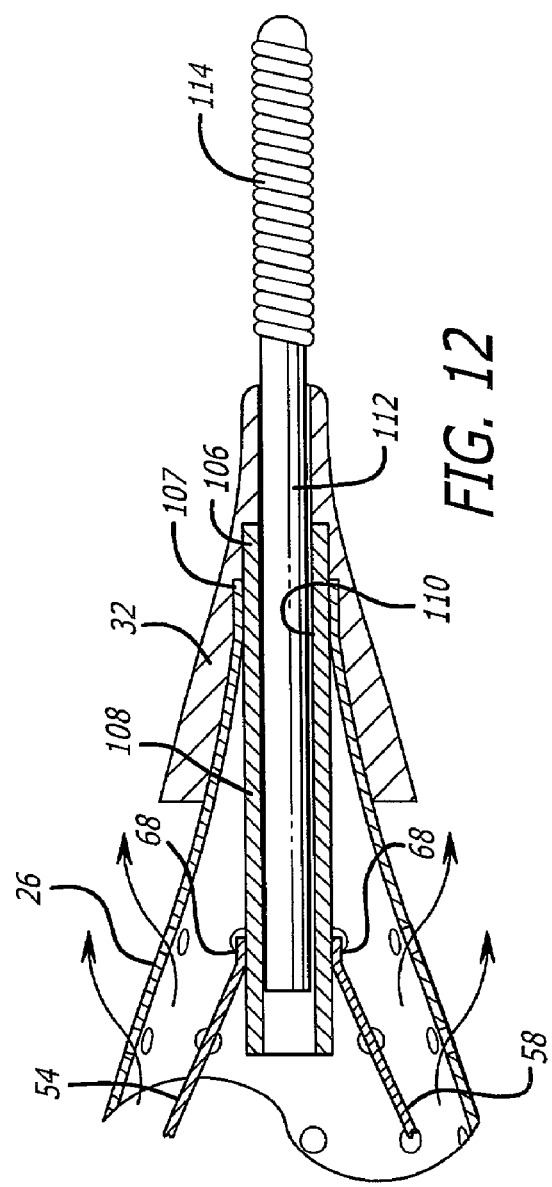

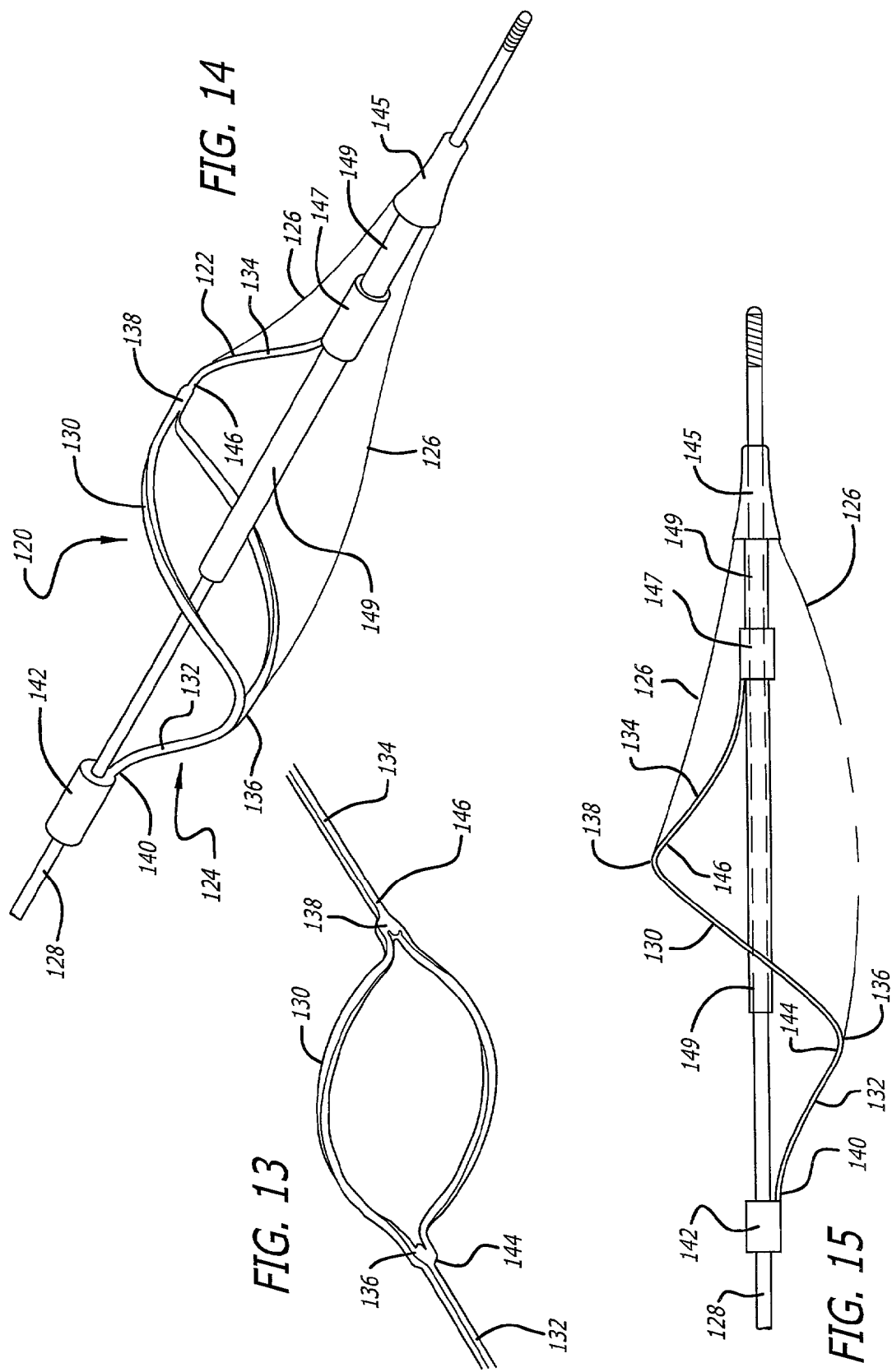

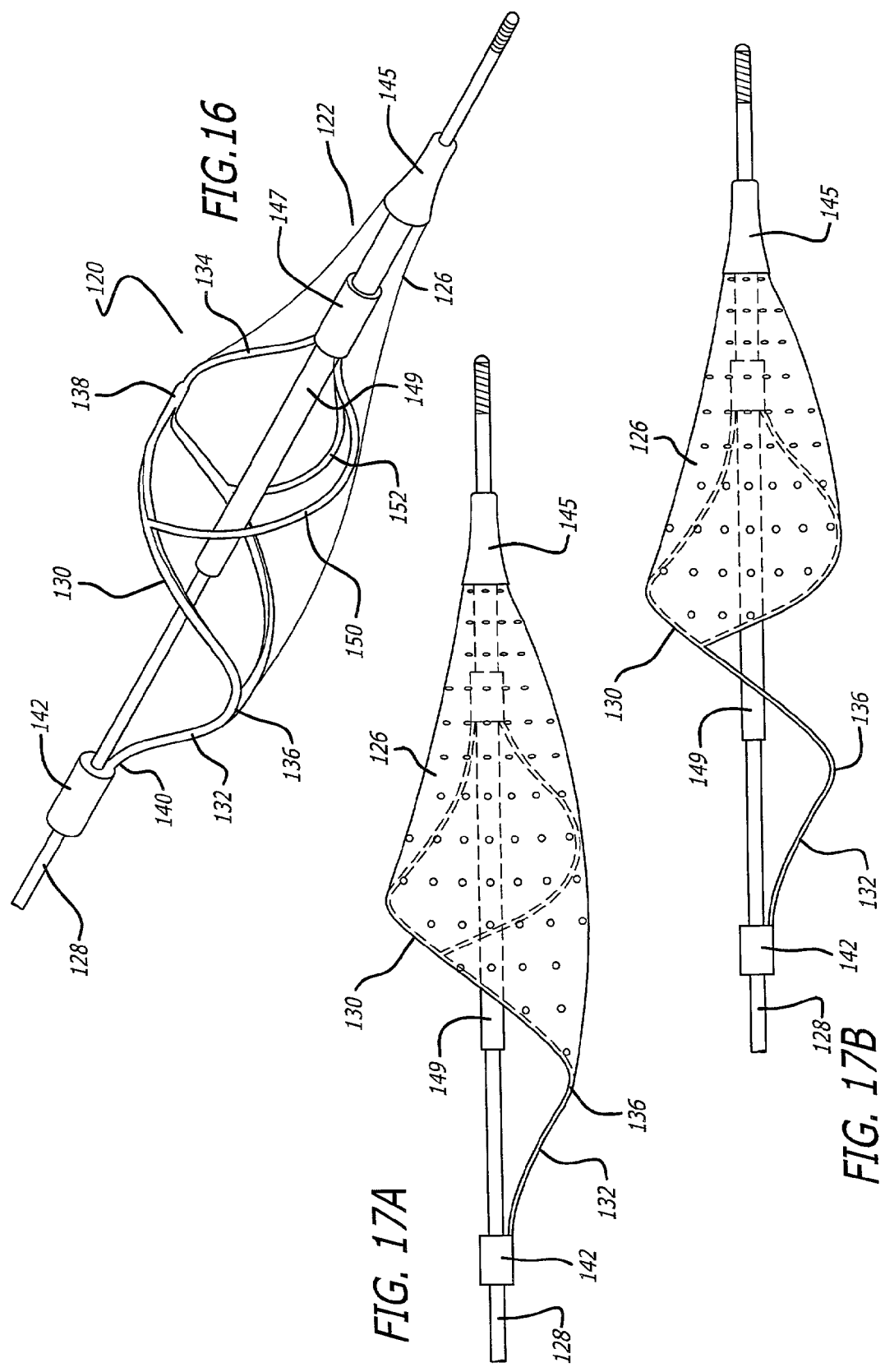

EXPANDABLE CAGES FOR EMBOLIC FILTERING DEVICES

BACKGROUND OF THE INVENTION

The present invention relates generally to filtering devices used when an interventional procedure is being performed in a stenosed or occluded region of a body vessel to capture embolic material that may be created and released into the vessel during the procedure. The present invention is more particularly directed to an embolic filtering device made with an expandable cage or basket having good flexibility and bendability.

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque that can travel downstream and lodge somewhere in the patient's vascular system. Pieces of plaque material are sometimes generated during a balloon angioplasty procedure and become released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the vacuum catheter and, as a result, enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, as mentioned above, there can be complications associated with such systems if the catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters vessel are attached to the distal end of a guide wire or guide wire-like member which allows the filtering device to be steered in the patient's vasculature as the guide wire is positioned by the physician.

Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

When a combination of an expandable filter and guide wire is utilized, it is important that the expandable filter portion remains flexible in order to negotiate the often tortuous anatomy through which it is being delivered. An expandable filter which is too stiff could prevent the device from reaching the desired deployment position within the patient's vasculature. As a result, there is a need to increase the flexibility of the expandable filter without compromising its structural integrity once in position within the patient's body vessel. Also, while it is beneficial if the area of treatment is located in a substantially straight portion of the patient's vasculature, sometimes the area of treatment is at a curved portion of the body vessel which can be problematic to the physician when implanting the expandable filter. If the expandable filter portion is too stiff, it is possible that the filter may not fully deploy within the curved portion of the body vessel. As a result, gaps between the filter and vessel wall can be formed which may permit some embolic debris to pass therethrough. Therefore, the filtering device should be sufficiently flexible to be deployed in, and to conform to, a tortuous section of the patient's vasculature, when needed.

What has been needed is an expandable filter assembly having high flexibility and bendability with sufficient strength and radiopacity to be successfully deployed within a patient's vasculature to collect embolic debris which may be released into the patient's vasculature.

SUMMARY OF THE INVENTION

The present invention provides a highly flexible cage (also referred to as a "basket") for use with an embolic filtering device designed to capture embolic debris created during the performance of a therapeutic interventional procedure, such as a balloon angioplasty or stenting procedure, in a body vessel. The present invention provides the physician with an embolic filtering device having high flexibility to be steered through tortuous anatomy, but yet possessing sufficient strength to hold open a filtering element against the wall of the body vessel for capturing embolic debris. An embolic filtering device made in accordance with the present invention is relatively easy to deploy, has good visibility under fluoroscopy, and has good flexibility and is conformable to the patient's anatomy.

An embolic filtering device made in accordance with the present invention utilizes an expandable cage made from a self-expanding material, for example, nickel-titanium (NiTi), and includes struts capable of expanding from a collapsed position or configuration having a first delivery diameter to an expanded or deployed position or configuration having a second implanted diameter. A filter element made from an embolic-capturing material is attached to the expandable cage to move between an expanded position and a deployed position.

In one aspect of the present invention, the enhanced flexibility and bendability of the embolic filtering device is achieved through the utilization of a unique cage design having a highly flexible and conformable circumferential member which is adapted to expand and conform to the size and shape of the body vessel. The expandable cage includes a proximal strut having an end connected to a guide wire and the other end attached to the circumferential member. A distal strut is attached to the circumferential member and has its other end attached to the guide wire. The filter element is attached to the circumferential member and will open and close as the expandable cage moves between its expanded, deployed position and its unexpanded, delivery position. The circumferential member is self-expanding and is made from a highly flexible material which allows it to conform to the particular size and shape of the body vessel. This high flexibility and conformability of the circumferential member allows the composite device to be deployed in curved sections of the patient's anatomy and other eccentric vessel locations having non-circular shaped lumens. This allows an embolic filtering device made in accordance with the present invention to be deployed in locations in the patient's anatomy which might not be otherwise suitable for stiffer filtering devices.

In another aspect of the present invention, bending regions formed on the circumferential member help to actuate the circumferential member between its unexpanded and expanded positions. In one aspect of the present invention, these bending regions are substantially U-shaped bends formed on the circumferential member at various locations along the member. While the circumferential member itself is self-expanding and capable of moving between these positions, the bending regions further enhance the actuation of the circumferential member between these positions. In one particular aspect of the present invention, the proximal strut is attached directly to this bending region. Likewise, a distal strut can be attached to a second bend section. In this fashion, a highly bendable and conformable cage can be produced which should conform to the particular shape of the body vessel once deployed.

In other aspects of the present invention, a pair of circumferential members can be utilized to create the expandable cage which maintains a high degree of bendability and conformability, but yet is sufficiently rigid enough to maintain the filtering element in an expanded position once the filtering device is fully deployed. The pair of circumferential members provides additional support to the filter element to help maintain the filter in the expanded configuration. Other aspects of the present invention utilize sets of three or four proximal struts and distal struts to form a larger expandable cage which still retains good bendability and conformability, yet possesses sufficiently radial strength when deployed to maintain proper wall apposition between the filter element and the body vessel.

In another aspect of the present invention, the expandable cage is made from a single, self-expanding wire adapted to open a filter element. The wire forms at least one loop in its expanded position to create an opening and helps to maintain the filter element in proper contact with the wall of the body vessel. Alternatively, a number of spirals can be formed on the wire cage to create a helical-type expandable cage capable of moving between an unexpanded and expanded position. In one form of the invention, the expandable cage can be utilized in conjunction with a delivery sheath which maintains the cage in its unexpanded position for delivery through the patient's vasculature. In another aspect of the invention, a delivery system which includes an actuating member is connected to the expandable cage to allow the cage to move between the expanded and collapsed positions by either rotation of the guide wire onto which the expandable cage is mounted or by moving the actuating member longitudinally along the guide wire. Accordingly, this can be accomplished by the physician at location outside of the patient.

The struts of the expandable cage can be set to remain in the expanded, deployed position until an external force is placed over the struts to collapse and move the struts to the collapsed position. One way of accomplishing this is through the use of a restraining sheath, for example, which can be placed over the filtering device in a coaxial fashion to contact the cage and move the cage into the collapsed position. The embolic filtering device can be placed in the patient's vasculature and remain there for a period of time. The filtering device can be attached to the distal end of an elongated member, such as a guide wire, for temporary placement in the vasculature to capture emboli created during an interventional procedure. A guide wire may be used in conjunction with the embolic filtering device when debris is to be filtered during an interventional procedure such as an angioplasty procedure or stenting procedure. The guide wire and filtering assembly, with the restraining sheath placed over the filter assembly, can be delivered through the patient's vasculature to the target location. Once the physician properly manipulates the guide wire into the target area, the restraining sheath can be retracted to deploy the basket into the expanded position. This can be easily performed by the physician by simply retracting the proximal end of the restraining sheath (located outside of the patient). Once the restraining sheath is retracted, the self-expanding properties of the cage cause the struts and circumferential members to move in a outward, radial fashion away from the guide wire to contact the wall of the body vessel. As the struts and circumferential member(s) expand radially, so does the filter element which will now be maintained in place to collect embolic debris that may be released into the bloodstream as the physician performs the interventional procedure. The guide wire can be used by the physician to deliver the necessary interventional device into the area of treatment. The deployed filter element captures embolic debris created and released into the body vessel during the interventional procedure. A retrieval sheath can be delivered over the guide wire to collapse the filter assembly for removal from the patient.

It is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

BRIEF DESCRIPTION OF THE DRAWINGS

FIG. 1 is a perspective view of an embolic filtering device with an expandable cage embodying features of the present invention.

FIG. 2 is a perspective view of the expandable cage of FIG. 1 in its expanded configuration with the filter element removed to better show the expandable cage.

FIG. 3 is an elevational view, partially in cross section, of the embolic filtering device of FIG. 1 as it is being delivered within a body vessel downstream from an area to be treated.

FIG. 4 is an elevational view, partially in cross section, similar to that shown in FIG. 3, wherein the embolic filtering device is deployed in its expanded position within the body vessel for filtering purposes.

FIG. 9 is a perspective view of another an embolic filtering device which uses an expand able cage embodying features of the present invention.

FIG. 10 is a side elevational view of a connecting strut having an S-shaped configuration which joins adjacent circumferential members together.

FIG. 11 is a side elevational view, partially in cross-section, of the distal end of the embolic filter assembly of FIG. 1.

FIG. 12 is a side elevational view, partially in cross-section, of the distal end of the embolic filter assembly of FIG. 9.

FIG. 13 is a perspective view of another embodiment of an expandable cage as formed from a tubular member which embodies features of the present invention.

FIG. 14 is a perspective view of an embolic filtering device which uses the expandable cage of FIG. 9 and embodies features of the present invention.

FIG. 15 is a side elevational view of the embolic filtering device of FIG. 10.

FIG. 16 is a perspective view of another embodiment of an embolic filtering device embodying features of the present invention.

FIG. 17A is a side elevational view of the filter member attached to the expandable cage of the embolic filtering device of FIG. 16.

FIG. 17B is a side elevational view showing an alternative method for attaching the filter member to the expandable cage of the embolic filter device of FIG. 16.

DETAILED DESCRIPTION OF THE PREFERRED EMBODIMENTS

Figure 5:
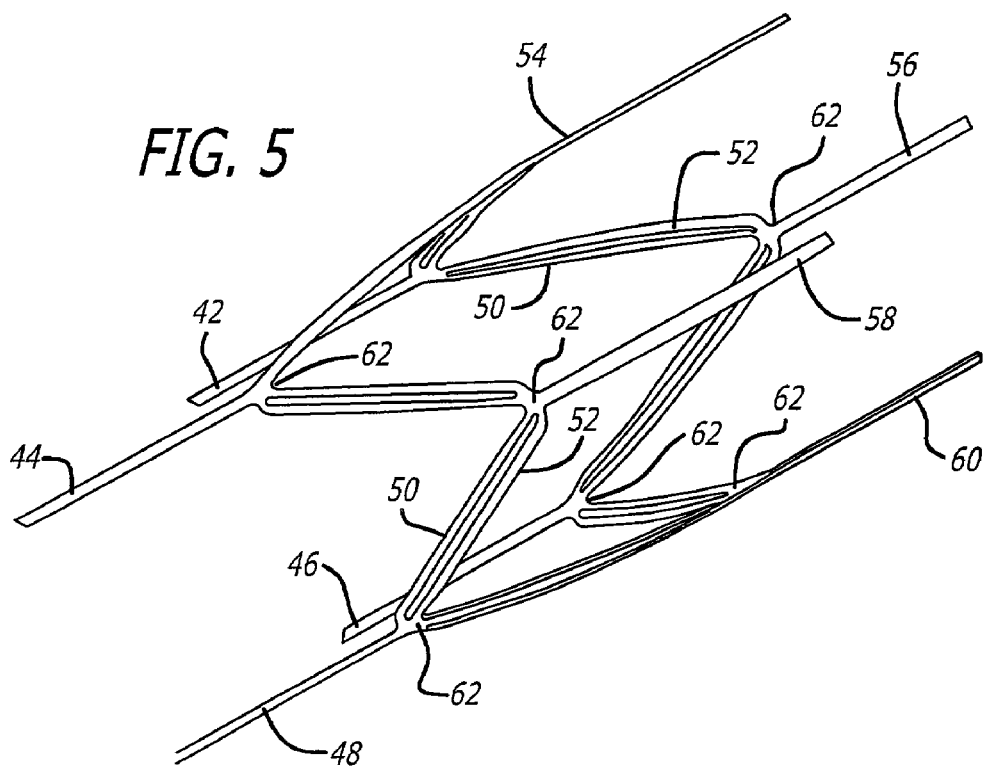
FIG. 5 is a perspective view of the expandable cage of FIGS. 1 and 2 as it is initially formed from a tubular member.

Turning now to the drawings, in which like reference numerals represent like or corresponding elements in the drawings, FIGS. 1 and 2 illustrate one particular embodiment of an embolic filtering device 20 incorporating features of the present invention. This embolic filtering device 20 is designed to capture embolic debris which may be created and released into a body vessel during an interventional procedure. The embolic filtering device 20 includes an expandable filter assembly 22 having a self-expanding basket or cage 24 and a filter element 26 attached thereto. In this particular embodiment, the expandable filter assembly 22 is rotatably mounted on the distal end of an elongated (solid or hollow) cylindrical tubular shaft, such as a guide wire 28. The expandable filter assembly could also be attached directly onto the guide wire, so as not to rotate independently of the guide wire. The guide wire has a proximal end (not shown) which extends outside the patient and is manipulated by the physician to deliver the filter assembly into the target area in the patient's vasculature. A restraining or delivery sheath 30 (FIG. 3) extends coaxially along the guide wire 28 in order to maintain the expandable filter assembly 22 in its collapsed position until it is ready to be deployed within the patient's vasculature. The expandable filter assembly 22 is deployed by the physician by simply retracting the restraining sheath 30 proximally to expose the expandable filter assembly. Once the restraining sheath is retracted, the self-expanding cage 24 immediately begins to expand within the body vessel (see FIG. 4), causing the filter element 26 to expand as well.

An obturator 32 affixed to the distal end of the filter assembly 32 can be implemented to prevent possible "snowplowing" of the embolic filtering device as it is being delivered through the vasculature. The obturator can be made from a soft polymeric material, such as Pebax 40D, and has a smooth surface to help the embolic filtering device travel through the vasculature and cross lesions while preventing the distal end of the restraining sheath 30 from "digging" or "snowplowing" into the wall of the body vessel.

In FIGS. 3 and 4, the embolic filtering device 20 is shown as it is being delivered within an artery 34 or other body vessel of the patient. Since the embolic filtering device made in accordance with the present invention possesses excellent bendability and flexibility, it will conform well to the shape of the vasculature while allowing the filter assembly to more easily negotiate a curved radius in the patient's vasculature.

Referring now to FIG. 4, the embolic filtering device 20 is shown in its expanded position within the patient's artery 34. This portion of the artery (FIG. 3) has an area of treatment 36 in which atherosclerotic plaque 38 has built up against the inside wall 40 of the artery 34. The filter assembly 22 is to be placed distal to, and downstream from, the area of treatment 36. For example, the therapeutic interventional procedure may comprise the implantation of a stent (not shown) to increase the diameter of an occluded artery and increase the flow of blood therethrough. It should be appreciated that the embodiments of the embolic filtering device described herein are illustrated and described by way of example only and not by way of limitation. Also, while the present invention is described in detail as applied to an artery of the patient, those skilled in the art will appreciate that it can also be used in other body vessels, such as the coronary arteries, carotid arteries, renal arteries, saphenous vein grafts and other peripheral arteries. Additionally, the present invention can be utilized when a physician performs any one of a number of interventional procedures, such as balloon angioplasty, laser angioplasty or atherectomy which generally require an embolic filtering device to capture embolic debris created during the procedure.

The cage 24 includes self-expanding struts which, upon release from the restraining sheath 30, expand the filter element 26 into its deployed position within the artery (FIG. 4). Embolic particles 27 created during the interventional procedure and released into the bloodstream are captured within the deployed filter element 26. The filter may include perfusion openings 29, or other suitable perfusion means, for allowing blood flow through the filter 26. The filter element will capture embolic particles which are larger than the perfusion openings while allowing some blood to perfuse downstream to vital organs. Although not shown, a balloon angioplasty catheter can be initially introduced within the patient's vasculature in a conventional SELDINGER technique through a guiding catheter (not shown). The guide wire 28 is disposed through the area of treatment and the dilatation catheter can be advanced over the guide wire 28 within the artery 34 until the balloon portion is directly in the area of treatment 36. The balloon of the dilatation catheter can be expanded, expanding the plaque 38 against the wall 40 of the artery 34 to expand the artery and reduce the blockage in the vessel at the position of the plaque 38. After the dilatation catheter is removed from the patient's vasculature, a stent (not shown) could be implanted in the area of treatment 36 using over-the-wire techniques to help hold and maintain this portion of the artery 34 and help prevent restenosis from occurring in the area of treatment. The stent could be delivered to the area of treatment on a stent delivery catheter (not shown) which is advanced from the proximal end of the guide wire to the area of treatment. Any embolic debris created during the interventional procedure will be released into the bloodstream and should enter the filter 26. Once the procedure is completed, the interventional device may be removed from the guide wire. The filter assembly 22 can also be collapsed and removed from the artery 34, taking with it any embolic debris trapped within the filter element 26. A recovery sheath (not shown) can be delivered over the guide wire 28 to collapse the filter assembly 22 for removal from the patient's vasculature.

Referring again to FIGS. 1 and 2, the expandable cage 24 includes four self-expanding proximal struts 42-48 which help to deploy the filter element 26 and the remainder of the expandable cage. These proximal struts 42-48 are coupled to a first circumferential member 50 which is adapted to move from the unexpanded delivery position (FIG. 3) to the expanded deployed position (FIG. 4). A second circumferential member 52 is, in turn, coupled to the first circumferential member 50. The deployment of the first and second circumferential members 50 and 52 results in the filter element 26 being placed against the wall 40 of the artery or other body vessel, even if the lumen of the body vessel is non-circular (FIG. 4). Four distal struts 54-60 are connected to the second circumferential member 52 and extend distally towards the obturator 32.

As can be seen in FIGS. 1 and 2, each circumferential member is formed in a zig-zag pattern which includes eight apexes to which the proximal and distal struts are attached. These apexes form eight bending regions 62 which enhance the bending of the circumferential member as it moves between the unexpanded and expanded positions. In the particular embodiment shown in FIG. 2, each bending region 62 is placed on the circumferential member approximately 45 degrees apart. Each of the proximal struts includes a first end 64 attached to the collar 65 which is rotatably mounted to the guide wire 28. The proximal struts may be attached directly onto the guide wire. Each proximal strut also includes a second end 66 connected to one of the bending regions of the first circumferential member 50. The bending regions 62 attached to the proximal struts are spaced approximately 90 degrees apart from each other along a circular diameter defined by the expanded circumferential member. Each of the distal struts, in turn, has a first end 68 connected to, and extending towards, the obturator 32 and a second end 70 attached to distally located bending regions on the second circumferential member. These distally located bending regions, in turn, are spaced approximately 90 degrees apart from each other and are offset 45 degrees from the proximally located bending regions.

Each of the bending regions is substantially U-shaped which help to create a natural bending point on the circumferential member. While the flexibility of the circumferential members is already high, these bending regions only help to increase the ability of the circumferential member to collapse or expand when needed. In this manner, the shape of the hinge regions creates a natural hinge that helps to actuate the expandable cage between the unexpanded and expanded positions. As can be best seen in FIG. 2, the U-shaped proximally located bending regions are positioned directly opposite the U-shaped portion of the distally located bending regions. The positioning of the direction of the U portion also enhances the ability of the circumferential member to bend. These circumferential members, while being quite bendable, nevertheless maintain sufficient radial strength to remain in the deployed position to hold the filter element 26 open in the body vessel for collecting embolic particles which may be entrained in the body fluid.

The shape of the bending regions are shown as substantially U-shaped portions, however, any one of a number of different shapes could also be utilized to create a natural bending point on the circumferential member. For example, a V-shaped region could also be formed and would function similarly to a U-shaped portion to facilitate the collapse and expansion of the circumferential member as needed. Alternative shapes and sizes of the bending regions also could be utilized without departing from the spirit and scope of the invention. Although eight bending regions are shown on each circumferential member, it should be appreciated that the number of different bending regions could be increased or decreased as needed. For example, it is possible to utilize only two bending regions, as is shown in the embodiment of the expandable cage of FIGS. 9-11, in order to facilitate bending. Additional bending regions also could be utilized in the event that additional proximal or distal struts are used to form the expandable cage. Moreover, different sizes, shapes and location of the bending regions can be utilized on any circumferential member.

Referring now to FIG. 5, the expandable cage 24 is shown as it appears after it has been cut from a tubular member, the process of which is disclosed in further detail below. As can be seen, the free ends of the proximal and distal struts are initially spread apart after being formed from the tubular member. The free ends of the struts can be attached to a collar, such as is shown in FIGS. 1 and 2, to allow the expandable cage to be mounted to an elongated member, such as a guide wire.

The free ends of the proximal and distal struts can be fastened to the collar using known bonding techniques, including, braising, soldering, welding, as well as adhesive bonding.

Figure 6:
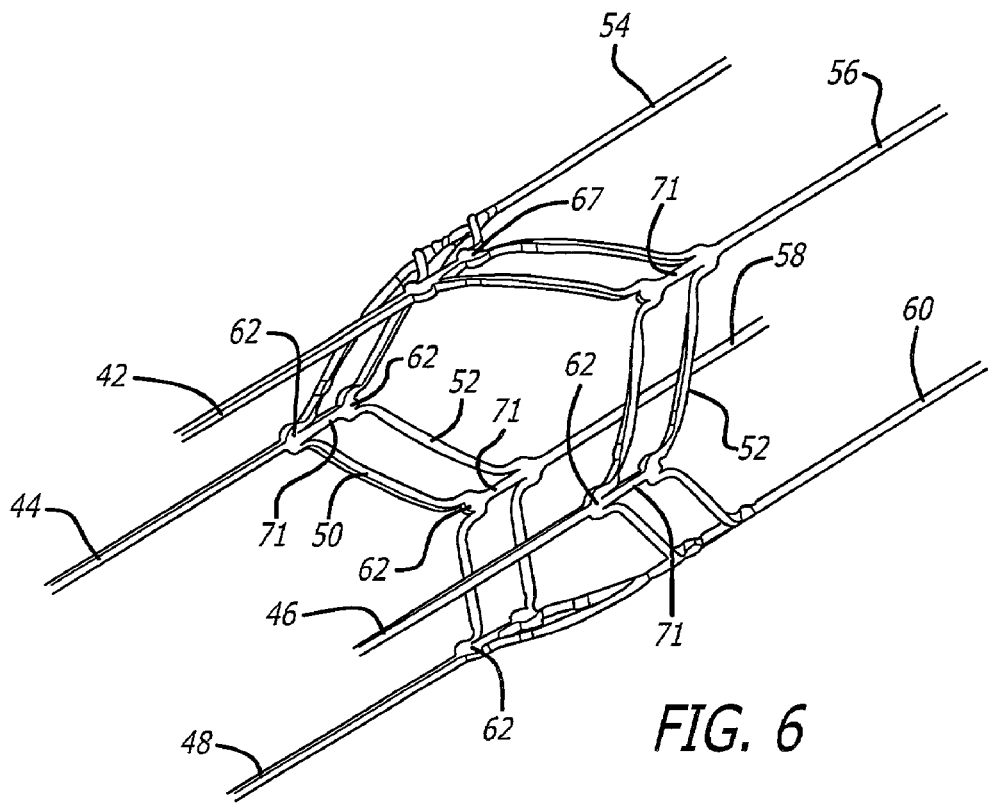
FIG. 6 is a perspective view of another embodiment of an expandable cage as formed from a tubular member which embodies features of the present invention.

Referring now to FIG. 6, a similar embodiment of the expandable cage 24 is shown. It should be appreciated that the expandable cage of FIG. 6 is also shown as it would be cut from a tubular member and that the free ends of the proximal and distal struts are not shown attached to a collar or an obturator. This design shows how the first and second circumferential members can be coupled to, and spaced apart, from each other by short connecting struts 71. These short connecting struts 71 create a larger basket and may help the circumferential members to expand since the circumferential members are not spaced as closely as they are in the embodiment shown in FIGS. 1-2.

The expandable cage 24 of the present invention is shown rotatably mounted to the distal end of the guide wire 28 to allow the entire filter assembly 22 to remain stationary once deployed in the body vessel. This feature prevents the filtering assembly from rotating against the wall of the body vessel in the event that the proximal end of the guide wire should be rotated by the physician during use. As a result, the possibility that the deployed filter assembly 22 could be rotated to cause trauma to the wall of the vessel is minimized. Referring again to FIGS. 1 and 2, a pair of stop fittings 72 and 74 are placed on the guide wire to maintain the collar 65, and hence the proximal end of the expandable cage 24, rotatably fixed to the guide wire 28. These stop fittings 72 and 74 allow the expandable cage 24 to spin on the guide wire while restricting the longitudinal movement of the cage on the guide wire. This particular mechanism is just one way in which the expandable cage 24 can be mounted to the guide wire 28. Alternatively, the expandable cage can be attached directly onto the guide wire so as not to rotate independently.

Figure 7:
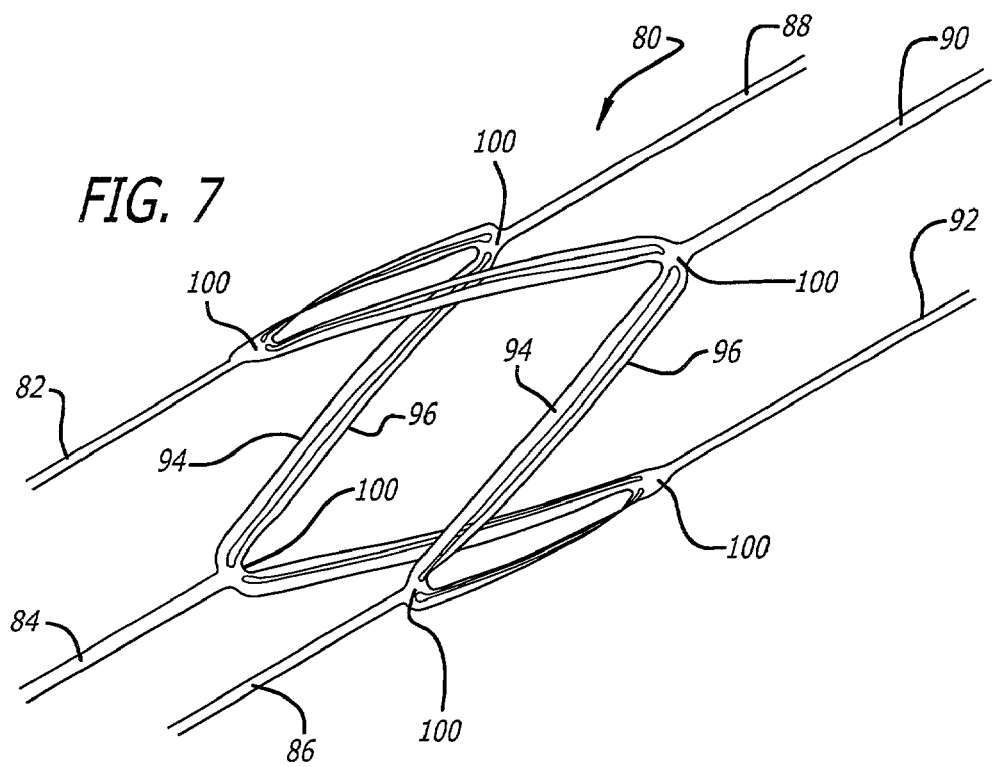
FIG. 7 is a perspective view of another embodiment of an expandable cage as formed from a tubular member which embodies features of the present invention.
Figure 8:
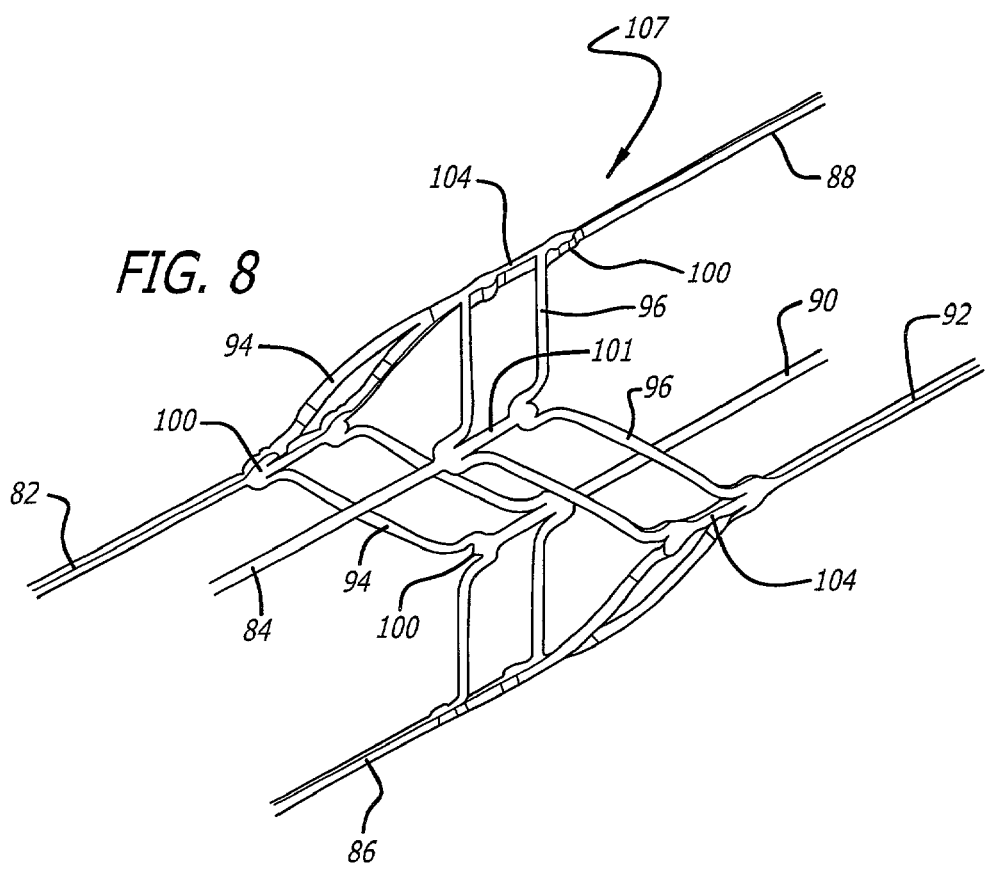
FIG. 8 is a perspective view of another embodiment of an expandable cage as formed from a tubular member which embodies features of the present invention.

Referring now to FIGS. 7 and 8, alternative embodiments of an expandable cage made in accordance with the present invention are shown. First, referring specifically to FIG. 7, the expandable cage 80 is shown having only three proximal struts 82-86 and three distal struts 88-92 attached to first and second circumferential members 94 and 96. It should be appreciated that this particular figure shows the expandable cage 80 as it would appear after being cut from a tubular member since the free ends of the proximal and distal struts are unconnected to a collar or obturator. Each circumferential member 94 and 96 has six apexes which form the bending regions 100 on the circumferential member. Each of the three proximally located bending regions are spaced approximately 120 degrees apart from each other and, likewise, the distally located bending regions are spaced approximately 120 degrees apart. It should be appreciated that this embodiment of the expandable cage functions in the same manner as the cage shown in FIGS. 1-5.

FIG. 8 shows a further embodiment of an expandable cage 102 which is similar to the embodiment shown in FIG. 7, except for the presence of short, connecting struts 104 which connect the first and second circumferential members 94 and 96 together. Likewise, this particular cage 102 is shown in its fully expanded position as it would appear after being cut from a tubular member with the free ends of the proximal and distal struts remaining unattached. This particular embodiment, as with the embodiment shown in FIG. 7, would require the ends of the struts to be attached to a collar, an obturator or some other structure to fully form the expandable cage. Alternatively, the ends of the struts of this embodiment, or any embodiment of the expandable cage, could be directly attached to the elongated member, such as a guide wire, directly if so desired. In this manner, the expandable cage would not be rotatably mounted to the guide wire, but would nevertheless be fixed thereto. In such an alternative embodiment of the embolic filtering device, only one end of the expandable cage, usually the proximal struts of the cage, would be physically and directly attached to the guide wire. The distal end of the cage would be capable of longitudinal movement to allow the cage to move between its unexpanded and expanded configurations.

An alternative embodiment of the embolic filtering device 20 is shown in FIG. 9. This particular embodiment of the embolic filtering device 20 includes an expandable filter assembly 22 having a self-expanding cage 24 and a filter element 26 attached thereto. The expandable filter assembly 22 is shown rotatably mounted on a distal end of an elongated shaft, such as guide wire 28. In this particular embodiment, the guide wire 28 does not extend through the expandable cage 24, is as shown in the embodiment of FIGS. 1 and 2, but rather, terminates at the distal most fitting 74 connected to the guide wire 28. In this manner, the filtering assembly 22 remains rotatably fixed to the guide wire 28 to provide the same features described above. The absence of the short segment of guide wire through the expandable cage may provide a lower profile to the composite filter assembly, if desired. The distal most end of the assembly includes a tip coil which allows the physician to steer the composite embolic filtering device/delivery sheath as is shown in FIG. 3.

Referring now to FIGS. 11 and 12, methods in which the ends of the distal struts of the embodiment of FIGS. 1 and 9 could be attached to the obturator 32 is shown. As can be seen in FIG. 11, the distal ends 68 are attached to a tubular member 106 which extends into the obturator 32. The ends 68 are attached to the outer surface 108 of the tubular member 106. The filter 26 tapers to a distal end 107 which is, in turn, bonded or otherwise adhesively attached to the outer surface 108 of this tubular member 106. Likewise, at least a portion of the tubular member is in contact with the obturator 32 and is adhesively bonded or otherwise affixed thereto. The inner surface 110 of the tubular member 106 can slide over the guide wire 28 and tip coil 114. Referring specifically now to FIG. 12, the method of attaching the distal struts of the embodiment of FIG. 9 is shown. This particular construction is very similar to the attachment depicted in FIG. 11. Since there is no continuous guide wire extending through the expandable cage 24, a short segment 112 of the guide wire would be adhesively bonded or otherwise attached to the inner surface 110 of the tubular member 106. The combination of elements forms an integral distal end for the filtering assembly which can move relative to the guide wire during usage.

The short connecting struts 71 utilized in conjunction with the different embodiments of the expandable cage can be a substantially straight segment, as is shown in FIGS. 6 and 8, or can be a non-linear shape which may help in deploying the embolic filter in a curved section of the patient's anatomy. Referring specifically to FIG. 10, an example of a non-linear connecting strut 71 which connects a first circumferential member 50 to a second circumferential member 52 is shown. As can be seen in FIG. 10, the non-linear connecting strut has a substantial S-shape capable of undergoing bending forces to increase the ability of the cage to bend within the anatomy in which it is deployed. The non-linear intermediate strut 71 of FIG. 10 is just one particular shape which could be used in conjunction with the present invention. It should be appreciated that other sizes and shapes of the connecting struts could be utilized in accordance with any of the embodiments of an expandable cage made in accordance with the present invention.

Referring now to FIGS. 13-15, an alternative embodiment of the embolic filter device 120 is shown which includes an expandable filter assembly 122 with an expandable cage 124. In this particular embodiment, the expandable cage 124 is a modification of the expandable cage shown in FIGS. 1-5. The filter assembly 122 includes the filter member (not shown) utilized to filter the embolic debris in the body vessel and a plurality of openings (not shown) through which the body fluid flows through while the embolic particles remain trapped in the pocket formed by the filter member. The filter member is shown as it would appear on the filter assembly 122 by the lines 126 which depicts the outer edge of the filter member. The filter assembly 112 is also shown attached to a guide wire 128 having a proximal end (not shown) extending outside of the patient's body which can be manipulated by the physician to steer the device into the target area in the patient's vasculature. This particular embodiment is self-expanding, as with the other embodiment shown in FIGS. 1-5, would be kept in a collapsed delivery position through the use of a sheath which would extend over the filter assembly (as is shown in FIG. 3) in order to deliver the device into the target area.

The expandable cage includes a single circumferential member 130 and a single proximal strut 132 and a single distal strut 134. The circumferential member 130 includes only a pair of bending regions 136 and 138 although it is still possible to utilize other bending regions. The use of a single proximal strut 132 reduces the amount of surface area of the struts that are placed in front of the opening of the filter assembly, thus minimizing the chances that emboli could collect on strut surfaces rather than being driven into the filter member. The use of a single distal strut also allows the device to be more flexible in the distal area where flexibility is needed when negotiating tortuous anatomy. It should be appreciated that a single circumferential member could be used in accordance with the present embodiment or additional circumferential members could be added to create a longer filtering assembly.

The proximal strut 132 has one end 140 attached to a collar 142 that is rotatably mounted onto the distal end of the guide wire. A pair of stop fittings (not shown) maintain the collar rotatably mounted to the distal end of the guide wire. Also, the filter can be attached directly onto the guide wire. The other end 144 of the proximal strut is in turn attached to the bending region 136 located on the circumferential member 130. The distal strut 134 includes one end 146 attached to the bending region 138 of the circumferential member 130 with the other end 148 attached to a collar 147 or tubular member 149 that extends proximally from the obturator 145. Alternatively, the method of attaching the distal strut to the obturator can be similar to the arrangement shown in FIG. 12.

Referring now to FIG. 16, an alternative design of the embolic filter device 120 is shown. This particular embodiment is similar to the one shown in FIGS. 13-15 except for the additional distal struts 150 and 152 which extend from the circumferential member 130 to the collar 147. As can be seen, these additional distal struts 150 and 152 are attached to the circumferential members at a point between the two bending regions 136 and 138 which are formed on the circumferential member 130. These additional distal struts 150 and 152 provide additional rigidity to the filter assembly 122. It should be appreciated that additional or less distal struts could be added to the expandable cage 124 to provide additional support and strength to the cage as needed. The filter member could be attached as shown in FIGS. 17A or 17B.

Figure 18:
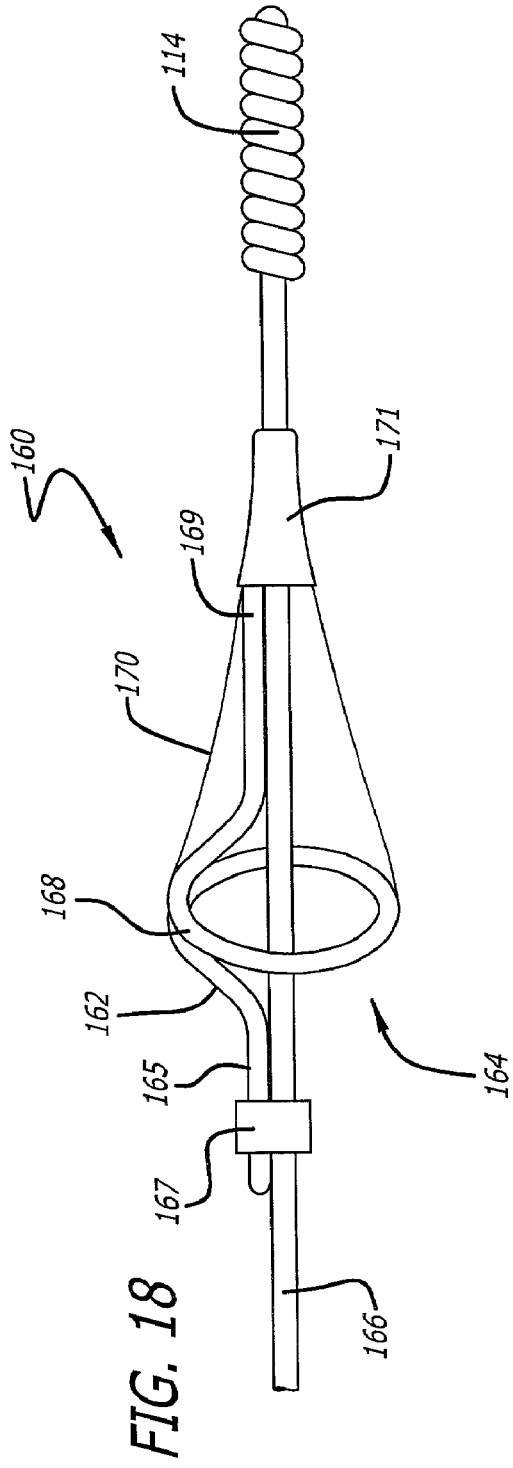
FIG. 18 is a side elevational view of another embolic filtering device with an expandable cage embodying features of the present invention.
Figure 19:
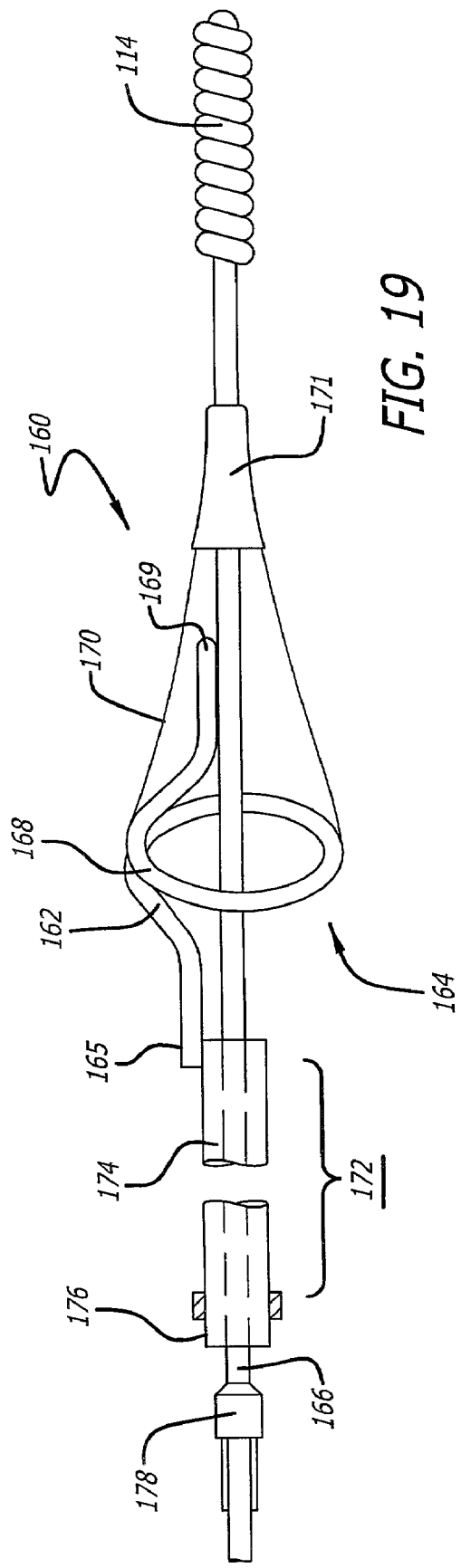
FIG. 19 is a side elevational view of the embolic filtering device of FIG. 13 showing one particular mechanism for moving the expandable cage between the unexpanded and expanded positions.

Referring now to FIGS. 18 and 19, an alternative embodiment of the embolic filter device 160 is shown. In this particular embodiment, the circumferential members have been replaced with a single, continuous wire 162 which forms the expandable cage 164. This cage 164 could be made from a lased tubular member in a manufacturing process similar to that for making the other embodiments of the expandable cage disclosed herein. The expandable cage 164 could be attached to the guide wire 166 as shown in FIG. 18. As can be seen in FIGS. 18 and 19, the expandable cage 164 forms at least one loop 168 when placed in the expanded position which results in a large the opening for the filter member, the outline of which is depicted by lines 170. This loop 168 remains substantially perpendicular to the guide wire 166 to enhance vessel apposition once placed in the body vessel.

The expandable cage 164 can be made from coldworked nickel-titanium or similar materials which will result in the wire 162 forming the loop 168 once placed in the expanded position. "X" marks have been placed on the wire 162 to designate areas which could be thinned to allow the wire 162 to more easily bend. The loop 168 formed by the wire 162 can be somewhat beneficial since it is directly perpendicular to the axis of the wire 166 to enhance the apposition of the filter assembly within the patient's body vessel. The proximal end 165 of the wire 162 can be attached to a collar 167 which is rotatably mounted to the guide wire 166. A pair of stop fittings (not shown) would be utilized to allow the cage 164 to spin freely on the guide wire in the same manner as the other embodiments disclosed herein. The other end of the wire 169 could, in turn, be connected to the obturator 171 in a manner similar to the attachment method described herein and shown in FIG. 15. In this manner, the distal end 169 of the expandable cage 164 would be movable longitudinally over the length of the guide wire 166 to enable it to move between its collapsed and open position.

Referring now to FIG. 19, the embolic filtering device 160 is shown as it would be mounted onto a movable actuating device 172 which is shown as a tubular member 174 in the figure. In this particular embodiment, the end 165 of the wire 162 is attached directly to the tubular member 174 with the other end 169 of the wire 162 being attached directly to the guide wire 166. This particular embodiment of the embolic filtering device 160 has certain features which allow the physician to manipulate the filtering assembly, i.e., expand and contract the filter member, as needed by either rotating the guide wire 166 or moving the tubular member 174 longitudinally along the length of the guide wire. This tubular member 174 extends proximally to a location where the physician can manipulate the proximal end 176 of the tubular member 174 in order to move the end 165 of the wire 162 longitudinally along the guide wire 166. In this manner, the expandable cage 164 will be capable of expanding or collapsing depending upon the direction in which the proximal end 176 of the tubular member 174 is manipulated. In use, the physician simply holds onto a torque device 178 attached to the guide wire 166 and manipulates the proximal end 176 of the tubular member 174 in order to collapse or deploy the expandable cage 164. In this manner, the physician moves the proximal end 176 longitudinally along the length of the guide wire 166 to either open or collapse the filter member. Alternatively, the physician can simply rotate the torque device 178, while keeping the proximal end 176 of the tubular member 174 stationary, to cause the end 169 of the wire 162 to turn with the guide wire 166. This action will cause the expandable cage 164 to either twist down onto the guide wire to collapse the filter or will open to the expanded position.

It should be appreciated that while the particular embodiments shown in FIGS. 18 and 19 depict a single loop 168 formed by the wire 162 to define the expandable cage 164, a plurality of loops could be formed to increase the size and the strength of the expandable cage 164 for a given application. Moreover, the size of the loop diameter can be progressively tapered to a smaller diameter as the loops approach the obturator 171 of the device so that a sleek tapered shape (helical) may be maintained. An alternative method for making this particular expandable cage 164 would include setting the particular shape of the loops onto a strand of wire, such as by coldwelding a nickel-titanium wire, to form the preformed shape of the loops. The loop would remain "set" in the expanded position until a collapsing force is placed on the expandable cage. In this manner, loops will be formed in the wire to define the shape of the cage once expanded.

The expandable cage of the present invention can be made in many ways. One particular method of making the cage is to cut a thin-walled tubular member, such as nickel-titanium hypotube, to remove portions of the tubing in the desired pattern for each strut, leaving relatively untouched the portions of the tubing which form the structure. The tubing may be cut into the desired pattern by means of a machine-controlled laser. The tubing used to make the cage could possible be made of suitable biocompatible material, such as spring steel. Elgiloy is another material which could possibly be used to manufacture the cage. Also, very elastic polymers possibly could be used to manufacture the cage.

The strut size is often very small, so the tubing from which the cage is made may have a small diameter. Typically, the tubing has an outer diameter on the order of about 0.020-0.040 inches in the unexpanded condition. Also, the cage can be cut from large diameter tubing. Fittings are attached to both ends of the lased tube to form the final cage geometry. The wall thickness of the tubing is usually about 0.076 mm (0.001-0.010 inches). As can be appreciated, the strut width and/or depth at the bending points will be less. For cages deployed in body lumens, such as PTA applications, the dimensions of the tubing may be correspondingly larger. While it is preferred that the cage be made from laser cut tubing, those skilled in the art will realize that the cage can be laser cut from a flat sheet and then rolled up in a cylindrical configuration with the longitudinal edges welded to form a cylindrical member.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The cage can be laser cut much like a stent is laser cut. Details on how the tubing can be cut by a laser are found in U.S. Pat. Nos. 5,759,192 (Saunders), 5,780,807 (Saunders) and 6,131,266 (Saunders) which have been assigned to Advanced Cardiovascular Systems, Inc.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about 0° C. and 20° C. in order to achieve superelasticity at human body temperature. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is less than approximately 0.5%. The breaking elongation is a minimum of 10%. It should be appreciated that other compositions of nickel-titanium can be utilized, as can other self-expanding alloys, to obtain the same features of a self-expanding cage made in accordance with the present invention.

In one example, the cage of the present invention can be laser cut from a tube of nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the cage such that it is super elastic at body temperature. The transformation temperature is at or below body temperature so that the cage is superelastic at body temperature. The cage is usually implanted into the target vessel which is smaller than the diameter of the cage in the expanded position so that the struts of the cage apply a force to the vessel wall to maintain the cage in its expanded position. It should be appreciated that the cage can be made from either superelastic, stress-induced martensite NiTi or shape-memory NiTi.

The cage could also be manufactured by laser cutting a large diameter tubing of nickel-titanium which would create the cage in its expanded position. Thereafter, the formed cage could be placed in its unexpanded position by back-loading the cage into a restraining sheath which will keep the device in the unexpanded position until it is ready for use. If the cage is formed in this manner, there would be no need to heat treat the tubing to achieve the final desired diameter. This process of forming the cage could be implemented when using superelastic or linear-elastic nickel-titanium.

The struts forming the proximal struts can be made from the same or a different material than the distal struts. In this manner, more or less flexibility for the proximal struts can be obtained. When a different material is utilized for the struts of the proximal struts, the distal struts can be manufactured through the lazing process described above with the proximal struts being formed separately and attached. Suitable fastening means such as adhesive bonding, brazing, soldering, welding and the like can be utilized in order to connect the struts to the distal assembly. Suitable materials for the struts include superelastic materials, such as nickel-titanium, spring steel, Elgiloy, along with polymeric materials which are sufficiently flexible and bendable.

The connecting struts utilized to connect one or more circumferential members together are shown generally as straight segments. However, it is possible to utilize non-linear shapes and sizes which may provide additional flexibility and bendability within the patient's anatomy. Additionally, it is possible to make these connecting struts out of materials which are different from the rest of the expandable cage to further increase flexibility if needed. As shown in FIG. 10, the connecting strut could be made in an S-shape which may provide additional flexibility in certain curved locations in the patient's anatomy. Moreover, the size and width of the strut could be varied from the remaining strut widths and thicknesses in order to promote additional flexibility. In a similar fashion, the bending regions formed on the circumferential members could also be formed with thinner and narrower strut widths than the remaining elements of the cage in order to enhance flexibility at these bending regions.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050-0.0050 inches. The wall thickness may vary depending on the particular material selected. The material can be made into a cone or similarly sized shape utilizing blow-mold technology or dip molding technology. The openings can be any different shape or size.

A laser, a heated rod or other process can be utilized to create to perfusion openings in the filter material. The holes, would of course be properly sized to catch the particular size of embolic debris of interest. Holes can be lazed in a spinal pattern with some similar pattern which will aid in the re-wrapping of the media during closure of the device. Additionally, the filter material can have a "set" put in it much like the "set" used in dilatation balloons to make the filter element re-wrap more easily when placed in the collapsed position.

The materials which can be utilized for the restraining sheath can be made from polymeric material such as cross-linked HDPE. This sheath can alternatively be made from a material such as polyolifin which has sufficient strength to hold the compressed strut assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

Further modifications and improvements may additionally be made to the device and method disclosed herein without departing from the scope of the present invention. Accordingly, it is not intended that the invention be limited, except as by the appended claims.

What is claimed is:

1. An embolic filtering device used to capture embolic debris in a body vessel, comprising:
   a guide wire; and
   a filter assembly disposed on the guide wire, the filter assembly including an expandable cage and filtering element attached to the cage, the cage being movable between an unexpanded and expanded position, the cage including a circumferential member which forms an inlet opening for the filtering element when placed in the expanded position, a single proximal strut having a first end attached to the circumferential member and a second end coupled to the guide wire, the proximal strut being configured to maintain the guide wire substantially centered through the inlet opening of the circumferential member when the cage is placed in the expanded position and a distal strut having a first end attached to the circumferential member and a second end coupled to the guide wire, wherein the circumferential member is adapted to sealingly contact the body vessel when placed in the expanded position to form a single inlet opening for capturing embolic debris.

2. The embolic filtering device of claim 1, wherein the circumferential member is adapted to be positioned at a slant with respect to the body vessel when placed in the expanded position.

3. The embolic filtering device of claim 1, wherein the cage is rotatably mounted to the guide wire.

4. The embolic filtering device of claim 1, further including a plurality of distal struts each having a first end attached to the circumferential member and a second end coupled to the guide wire.

5. The embolic filtering device of claim 1, wherein the proximal strut and the distal strut maintain the guide wire substantially centered in the circumferential member when the cage is placed in the expanded position.

6. An embolic filtering device used to capture embolic debris in a body vessel, comprising:
   a guide wire; and
   a filter assembly disposed on the guide wire, the filter assembly including an expandable cage and filtering element attached to the cage, the cage being movable between expanded and collapsed positions, the cage including a single circumferential member forming an oval-shaped inlet opening placed in the expanded position, a single proximal strut having a first end attached to the circumferential member and a second end attached to the guide wire, at least one distal strut having a first end attached to the circumferential member and a second end attached to the guide wire, the guide wire extending through the inlet opening of the circumferential member wherein the proximal strut being configured to maintain the guide wire substantially centered through the inlet opening of the circumferential member when the cage is placed in the expanded position.

7. The embolic filtering device of claim 6, wherein the second end of the proximal strut is rotatably mounted to the guide wire.

8. The embolic filtering device of claim 6, wherein the distal strut helps to maintain the guide wire substantially centered in the circumferential member when the cage is placed in the expanded position.

9. The embolic filtering device of claim 6, wherein the second end of the distal strut is rotatably attached to the guide wire.

10. The embolic filtering device of claim 9, further including a second distal strut having a first end attached to the circumferential member and a second end attached to the guide wire.

11. An embolic filtering device used to capture embolic debris in a body vessel, comprising:
   a guide wire; and
   a filter assembly disposed on the guide wire, the filter assembly including an expandable cage and filtering element attached to the cage, the cage being movable between expanded and collapsed positions, the cage including a single circumferential member forming an oval-shaped inlet opening placed in the expanded position, the circumferential member having a proximal bending region and a distal bending region formed thereon, a proximal strut having a first end attached to proximal bending region and a second end attached to the guide wire, a distal strut having a first end attached to the distal bending region and a second end attached to the guide wire, the guide wire extending through and substantially centered in the inlet opening of the circumferential member.

12. The embolic filtering device of claim 11, wherein the second end of the proximal strut is rotatably mounted to the guide wire.

13. The embolic filtering device of claim 11, wherein the proximal and distal struts help to maintain the guide wire substantially centered in the circumferential member when the cage is placed in the expanded position.

14. The embolic filtering device of claim 11, wherein the second end of the distal strut is rotatably attached to the guide wire.

15. The embolic filtering device of claim 11, further including a second distal strut having a first end attached to the circumferential member and a second end attached to the guide wire.

* * * * *